United States Patent [19]

Valdès Sosa et al.

[11] Patent Number: 5,307,807
[45] Date of Patent: May 3, 1994

[54] METHOD AND SYSTEM FOR THREE DIMENSIONAL TOMOGRAPHY OF ACTIVITY AND CONNECTIVITY OF BRAIN AND HEART ELECTROMAGNETIC WAVES GENERATORS

[75] Inventors: Pedro A. Valdès Sosa, La Lisa; Jorge J. Riera Diaz, Havana; Jorge B. Bayard, Havana; Rolando J. Biscay Lirio, Havana; Sara L. Gonzalez Andino; Rolando G. de Peralta Menéndez, both of La Lisa; Roberto D. Pascual Marqui, Havana, all of Cuba

[73] Assignee: Centro de Neurociencias de Cuba, Cuba

[21] Appl. No.: 849,594

[22] Filed: Mar. 11, 1992

[30] Foreign Application Priority Data

Mar. 15, 1991 [CU] Cuba ................................ 44/91

[51] Int. Cl.$^5$ ................................ A61B 5/05
[52] U.S. Cl. ........................ 128/653.1; 128/731; 324/244; 324/260
[58] Field of Search ............ 128/653.1, 731; 606/130; 324/248, 244, 245, 260

[56] References Cited

U.S. PATENT DOCUMENTS

| | | |
|---|---|---|
| 4,201,224 | 5/1980 | John . |
| 4,408,616 | 10/1983 | Duffy et al. . |
| 4,416,288 | 11/1983 | Freeman . |
| 4,417,592 | 11/1983 | John . |
| 4,591,787 | 5/1986 | Hoeing . |
| 4,736,751 | 4/1988 | Gevins et al. . |
| 4,753,246 | 6/1988 | Freeman . |
| 4,913,160 | 4/1990 | John . |
| 4,949,725 | 8/1990 | Raviv et al. ............ 128/731 |
| 4,977,896 | 12/1990 | Robinson et al. ........ 128/653.1 |
| 4,991,579 | 2/1991 | Allen ................ 128/653.1 |
| 4,995,395 | 2/1991 | Ilmoniemi et al. ....... 128/653.1 |

FOREIGN PATENT DOCUMENTS 2622990 5/1990 France .

OTHER PUBLICATIONS

S. J. Williamson et al; *Biomagnetism;* Journal of Magnetism and Magnetic Materials; 22 (1981); pp. 129-201.

*Primary Examiner*—Lee S. Cohen
*Assistant Examiner*—Brian L. Casler
*Attorney, Agent, or Firm*—Bacon & Thomas

[57] ABSTRACT

A method and system for the localization and characterization of the generators of human brain electromagnetic physiological activity includes a set of bioelectromagnetic amplifiers, sensorial stimulators, and a computer based system for signal analog to digital conversion and recording. Sufficient statistics, including higher order statistical moments, for event related components are computed from the recorded signals, either in the time, frequency, or time-frequency domain, retaining stationary, non-stationary, linear, and non-linear information. The localizations, orientations, activities, and connectivities of the generators are obtained by solving the inverse problem using sufficient statistics under anatomical and functional constraints. Realistic head geometry and conductivity profiles are used to transform the measurements into infinite homogeneous medium measurements, through use of ananatomical deconvolution operator, thus simplifying optimally inverse solution computations. Goodness of fit tests for the inverse solution are provided. Generator characteristics are visually displayed in the form of three and two dimensional head images, and optionally include probability scaled images obtained by comparing estimated generator characteristics with those of a normal population sampled and stored in a normative data base.

35 Claims, 3 Drawing Sheets

METHOD AND SYSTEM FOR THREE DIMENSIONAL TOMOGRAPHY OF ACTIVITY AND CONNECTIVITY OF BRAIN AND HEART ELECTROMAGNETIC WAVES GENERATORS

BACKGROUND OF THE INVENTION

1. Field of the Invention

The present invention relates to electronic computerized medical instruments and more particularly to the localization and characterization of the generators of brain and heart electric and magnetic activity by a non-invasive computerized method and system.

2. Description of Related Art

The determination of the three dimensional localization and of the temporal activity of the neuronal generators which give place to waveshapes, in an electroencephalogram (EEG) and an magnetoencephalogram (MEG) related to pathologies of the central nervous system (CNS), constitutes an important medical problem. Such knowledge can be helpful in producing more precise diagnostics in diverse neuropsychiatric pathologies and in determining more efficient treatments. A typical example is the study of the focus location followed by its sequential propagation in epilepsies that are being evaluated for surgical treatment.

The EEG and the MEG both have their common origin in the ionic currents produced by the cellular elements (the neurons) composing the CNS. The total current density vector field is determined by the vectorial additive combination of all of the elementary currents. The simultaneous activation of a large number of such elements, together with an adequate geometrical distribution, produces resulting electric potentials and magnetic fields which can be measured outside the head. In the transformation process from total current density to measurable external fields, the effects of the volume conductor properties of the different tissues composing the head must be taken into account: brain, meninges, cerebral spinal fluid, skull, and scalp.

The resulting measured fields have the characteristics of a stochastic process, which can be described either in the frequency domain or in the temporal domain, as a function of the statistical moments. In the case of a Gaussian process, first and second order moments give an exhaustive description.

The neural elements which generate a given EEG or MEG component may be localized on a small cortical area ("concentrated generator") or may, on the other hand, be widely distributed in different parts of the CNS ("diffuse generator"). The determination of the spatial distribution of the generators and of the multivariate statistical moments describing their interactions is very important.

For a number of decades electric potential measurements of the CNS have been performed by means of electrodes placed on the scalp. Much experience has accumulated on the practical utility of the visual inspection of the EEG in the diagnostics and treatment of patients with neuropsychiatric diseases. More recently, brain magnetic fields have been measured (U.S. Pat. No. 4,591,787), offering complementary information to that obtained from the EEG.

The current state of the art, as reflected in U.S. Pat. Nos. 4,201,224; 4,408,616; and 4,417,592 is summarized as follows. Quantitative analysis of brain electric activity by means of digital signal processing methods (QEEG) allows an objective evaluation of the functioning of the CNS. The signal recorded at each electrode is summarized by means of a set of descriptive parameters (DPs), based on stochastic process modeling. The DPs reflect the normal and pathological functioning of the CNS. Topographic maps based on the DPs are clinically useful, and even more so when statistically compared to a normative data base.

However, this analysis method generates an excessively large number of DPs, thus making quite difficult the evaluation of a particular patient. Moreover, the method does not attempt to localize the generators responsible for the measured DPs, thus limiting the clinical usefulness and contributing to the excessive redundancy of the DPs due to volume conduction effects. Finally, EEG is limited to the study of second order moments in the frequency domain, which means that the EEG has been implicitly assumed to be a Gaussian stochastic process, despite evidence revealing the non-linear nature of such signals.

In U.S. Pat. No. 4,913,160 a method for the reduction of the dimensionality of the DPs is proposed based on principal components (PCs) computation. This procedure produces minimum sets of linear combinations of the original DPs, with optimum descriptive properties, but which are meaningless in terms of the underlying neuronal generators and their localization. Furthermore, this method does not take into account the non-linear nature of the original signals.

An improvement in the usefulness of QEEG has been achieved by means of biophysical models which take into account the behavior of the electromagnetic fields produced by current sources in a complex volume conductor such as the human head. In this sense, U.S. Pat. Nos. 4,416,288; 4,753,246; and 4,736,751 propose procedures for eliminating the distortion effects due to the volume conductor. However, they do not deal with the spatial characterization of the generators.

Several attempts have been made to fit equivalent dipoles to measured fields in order to represent, albeit approximately, concentrated generators, either in the time domain or in the frequency domain. These procedures are based on the minimization of a certain distance criterion between the measurements and the theoretical field values due to a current dipole inside a volume conductor model of the head.

This type of procedure for source localization, based on first order moment data, does not take into account the existence of diffuse generators, nor the existence of other sources of "spatial noise". Furthermore, a statistical method for testing the goodness of fit of the source model is not provided. On the other hand, there is a fundamental limit on the number of dipoles that can be estimated, the maximum number being roughly equal to the number of electric or magnetic signals divided by six.

In French patent 2,622,990, several improvements are achieved by using frequency domain second order moment data, in the form of coherence matrices. An estimation method for the cross spectral spatial noise matrix is proposed, under the assumption of interelectrode independence, the method thus being statistically equivalent to the classical factor analysis model. The eigenvectors of the common factor space are then used for determining the concentrated generators (as many as the number of common factors).

However, empirical and theoretical evidence points towards a diffuse generator model for spatial noise, producing a structured cross spectral noise matrix for EEG and MEG. This explains why the proposed noise elimination method under the interelectrode independence assumption gives incorrect results. In such a case computations based on coherence matrices are not justified. Furthermore, dipole fitting methods applied to second order moment data or to eigenvector data are not equivalent. Finally, interactions between generators, neither linear nor non-linear, are taken into account in the eigenvector dipole fitting approach.

SUMMARY OF THE INVENTION

The objective of the present invention is a method and system for the characterization of both concentrated and diffuse generators of the EEG and MEG, based on all the statistical information available in these signals, in the form of statistical moments of all orders, in the time or frequency domain. The invention will allow the detection and estimation of the effect of the diffuse generators on the EEG and MEG. Also, it will allow the estimation of an increased number of concentrated generators, together with their linear and non-linear interactions.

In accordance with a first aspect of the invention there is provided a method for the three dimensional tomography of activity and connectivity of brain electromagnetic waves generators, said method including:

a) Attaching or approximating a set of electrodes and magnetic sensors to the scalp of an experimental subject to detect brain electromagnetic physiological activity in the form of an electroencephalogram (EEG) and a magnetoencephalogram (MEG), and measuring the exact positions of the electrodes and sensors with respect to a reference coordinate system determined by certain anatomical landmarks of the subject's head;

b) Amplifying the said electromagnetic signals detected at each electrode and sensor;

c) Obtaining on-line digital spatio-temporal signals, consisting of the EEG and MEG, by connecting analog-digital converters to each amplifier, and digitizing all data as it is gathered, under the control of a central experimental program;

d) Optional presentation of visual, auditory, and somato-sensorial stimulation to the experimental subject during EEG and MEG recording, carried out under the control of the central experimental program;

e) Optional recording and identification of responses produced by the experimental subject during EEG and MEG recording, for the inclusion of fiducial markers in the recording, and for the modification of the central experimental program;

f) Optional real-time detection of spontaneous events in the EEG and MEG produced by the experimental subject during recording, for the inclusion of fiducial markers in the recording, and for the modification of the experimental program;

g) Determination of a parametric description for the anatomy of the experimental subject's head (parametric geometry), by means of: i) exact computations based on anatomical or functional image processing of the subject's head, or ii) approximate computations based on a small set of anatomical measurements and comparison with a data base of normal and abnormal variability;

h) Using the parametric geometry for constructing a head phantom with all the volume conductor properties of the real head;

i) Performing EEG and MEG measurements on the head phantom due to known current dipoles located in the corresponding neural tissue volume, for determining the linear operator which transforms original EEG and MEG measurements into equivalent infinite homogeneous medium measurements (anatomical deconvolution);

j) Using the parametric geometry for determining anatomical and functional constraints for the localizations, orientations, activities, and connectivities of the brain electromagnetic waves generators (generator constraints);

k) Digital preprocessing of the EEG and MEG for artifact and noise elimination, and for the separation of EEG and MEG samples related to the fiducial markers, for obtaining event related components (ERCs);

l) Statistical analysis of the ERCs for determining the most adequate numerical description of the spatio-temporal properties in terms of sufficient statistics;

m) Computation of the activities and connectivities of the ERCs generators, based on the static solution to the inverse electromagnetic problem, under the above-mentioned generator constraints, using said sufficient statistics for the ERCs transformed to an infinite homogeneous medium by means of the anatomical deconvolution;

n) in case the generator constraints do not allow a unique solution to the inverse problem, the number of ERCs generators should be decreased sufficiently to allow for the proper identifiability of the inverse problem;

o) Statistical evaluation of the goodness of fit of the inverse solution, taking into account the existence of colored spatial and temporal noise, and including statistical hypotheses testing on the absence of activity and connectivity of the ERCs generators;

p) Optional computation of multivariate distances between ERCs generators characteristics (localizations, orientations, activities, and connectivities) of the experimental subject and of a normal population as determined from a normative data-base;

q) Visual display of three dimensional and two dimensional images corresponding to the localizations, orientations, activities, and connectivities of the ERCs generators, and the optional display of the multivariate distances.

In accordance with a second aspect of the invention there is provided a system for the three dimensional tomography of activity and connectivity of brain electromagnetic waves generators, including:

a) A set of electrodes and magnetic sensors adapted to be attached or approximated to the scalp of an experimental subject for the detection of brain electromagnetic physiological activity in the form of electroencephalogram (EEG) and magnetoencephalogram (MEG) electromagnetic signals, and means for measuring the exact positions of the electrodes and sensors with respect to a reference coordinate system determined by certain anatomical landmarks of the subject's head;

b) Means for the amplification electromagnetic signals detected at each electrode and sensor;

c) Means for obtaining on-line digital spatio-temporal signals consisting of EEG and MEG signals;

d) Means for the presentation of visual, auditory, and somato-sensorial stimulation to the experimental subject during EEG and MEG recording;

e) Means for recording the vocal or movement responses produced by the experimental subject during EEG and MEG recording;

A central digital computer subsystem, consisting of a multitasking processor or a set of distributed processors, that includes:

Means for reading the experimental subject's image data in the form of CAT scan images, NMR images, or in the form of a small set of anatomical measurements, and means for computing and storing the descriptive parametric geometry, the anatomical deconvolution operator, and the generator constraints;

Means for constructing a head phantom based on the descriptive parametric geometry, and means for the implantation of current dipoles in the corresponding neural tissue volume of the phantom;

Means for programming and for the control of experiments that comprise stimulation of the experimental subject, recording of the subject's responses, detection and recording of special EEG and MEG events, and simultaneous recording of the digitized electromagnetic signals;

Means for pre-processing the recorded electromagnetic signals for artifact and noise elimination;

Means for estimating event related components (ERCs);

Means for computing the ERCs sufficient statistics;

Means for estimating the additive non-white spatio-temporal noise due to diffuse generators;

Means for performing tests of hypotheses about the goodness of fit of the estimated inverse solution;

Means for estimating the localizations, orientations, activities, and connectivities of the ERCs generators;

Means for comparing the ERCs generators characteristics with a normative data base and means for computing multivariate metrics;

Means for the visual display of ERCs generators characteristics and of the multivariate metrics.

BRIEF DESCRIPTION OF THE DRAWINGS

In order that the invention be better understood, further detailed description follows with reference to accompanying drawings in which.

DETAILED DESCRIPTION OF THE PREFERRED EMBODIMENTS

Figure 1:
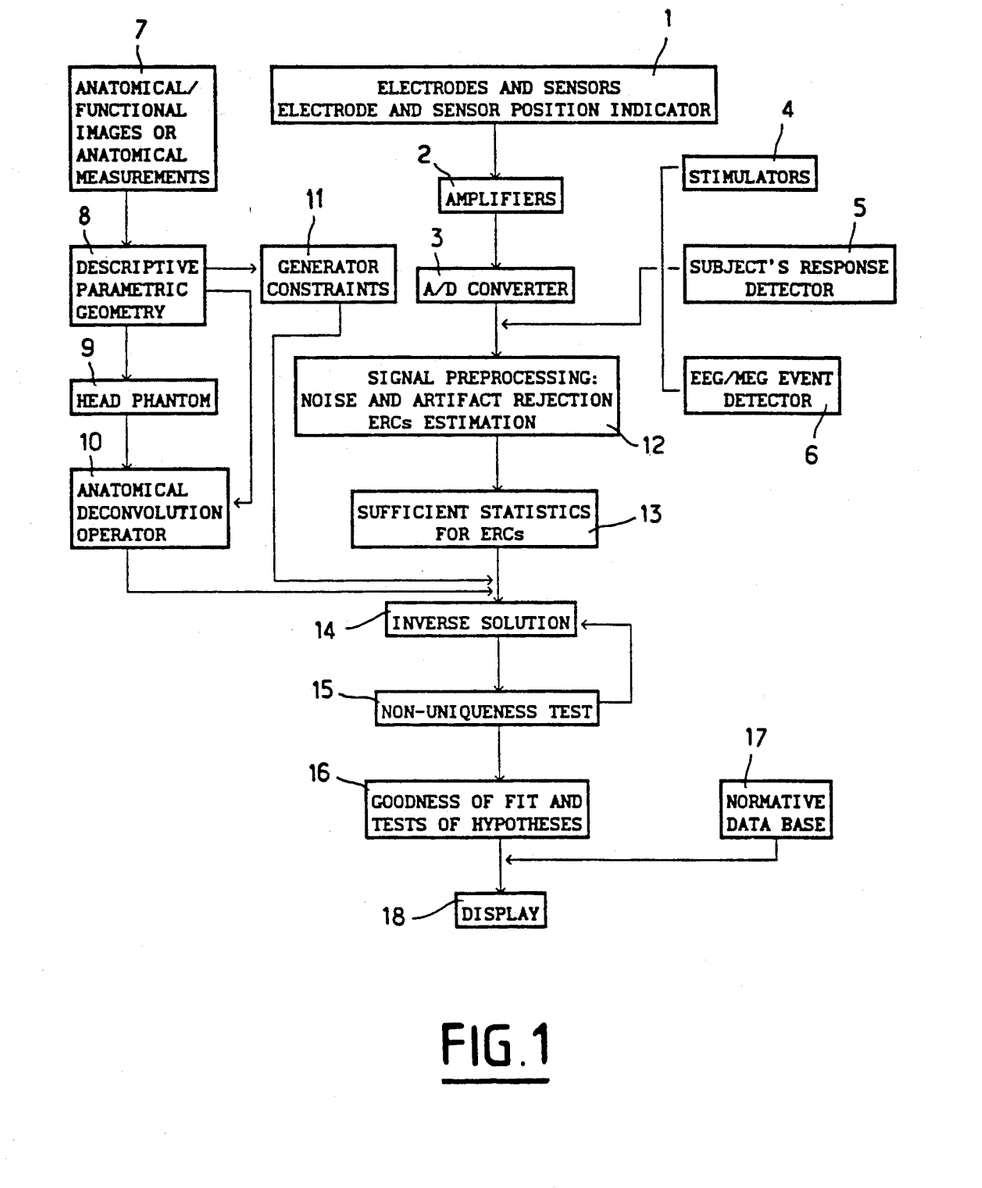
FIG. 1) is a schematic drawing of one embodiment of the present invention.

A plurality of sensors (1) (electrodes for EEG, magnetometers or gradiometers for MEG) are placed on or in proximity to the experimental subject's scalp, for the detection of brain electromagnetic signals, which are generated due to neuronal sources. The sensors are placed in order to maximize the amount of information about the generators. Due to variability of head shape and size in the human population, measurements of the exact positions of the sensors are required, with respect to a reference coordinate system determined by certain anatomical landmarks of the individual subject's head.

The electromagnetic signals are amplified (2) to the dynamic range of an analog to digital converter (3), which converts the signals into numbers that are stored in the memory of a digital computer.

The recording of electromagnetic signals is carried out according to a central experimental plan. During recording, the experimental subject can optionally be presented with visual, auditory, and somato-sensorial stimulation (4), with fiducial markers being added to the recording in the usual manner for later identification. Stimulation can be presented in the form of videogames. At the same time, responses produced by the experimental subject (5) in the form of vocalizations or body movements can be recorded and identified, and the spontaneous events in the EEG and MEG produced by the experimental subject as he or she makes the responses can optionally be used to change the experimental plan. The events can be paroxistic events or alpha rhythm desynchronization events, and the events can either be defined deterministically, statistically, or in terms of fuzzy logic.

Anatomical and functional information about the head, including aspects such as geometry of the different constituent tissues (e.g., brain, skull, scalp), location and orientation of the cortex and of other neuronal aggregates, is summarized in what is here termed descriptive parametric geometry (8). Each surface boundary can in general be expressed as an implicit function $F(x,y,z)=0$, where the variables x, y, and z represent common cartesian coordinates. The descriptive parametric geometry of an experimental subject consists of the finite set of coefficients $\{C_{mijk}\}$ used in approximating each boundary m (m=1,2, ..., $N_b$; where $N_b$ is the number of boundaries) in terms of an expansion of the form:

$$\sum_i \sum_j \sum_k C_{mijk} B_i(x) B_j(y) B_k(Z)$$

where $\{B_n\}$ is a finite set of $R \rightarrow R$ basis functions (n=1,2, ... $N_f$; $N_f$ is number of basis functions).

For each boundary, the expansion is fitted (in a least squares sense) to data from anatomical images (7) (e.g., CAT images or NMR images) or from functional images (e.g., PET images or SPECT images) of the experimental subject's head:

$$\underset{C}{\text{Min}} \left[ \sum_u \left( F_m(X_u, Y_u, Z_u) - \sum_i \sum_j \sum_k C_{mijk} B_i(X_u) B_j(Y_u) B_k(Z_u) \right)^2 \right]$$

where u=1, 2, ..., $M_m$; and $M_m$ is the number of sampled points on the m-th boundary. Alternatively, the expansion coefficients can be statistically predicted from a minimum set of easily measured anatomical parameters (7) by means of the information contained in a normative data base with a representative sample of experimental subjects covering the typical population:

$$C_{mijk} = G_{mijk}(\theta)$$

where $G_{mijk}$ is the statistically estimated $R^s \rightarrow R$ function, and $\theta \in R^s$ is the anatomical measurement parameter vector.

Important basis functions B to be used are:

a) The Fourier basis $B_n(v) = \exp(iv\omega_n)$, where $i = (-1)^{\frac{1}{2}}$, and v, $\omega_n \in R$.

b) The Karhunen-Loeve basis for each type of boundary surface.

c) Spatial spline bases.

The descriptive parametric geometry previously explained can be used for computing the anatomical deconvolution operator $\{D, E\}$ (10), which is defined in the following equations:

$$V_\infty = DV, \text{ and } B_\infty = B + EV$$

where $V \in R^p$ and $B \in R^q$ are the electric potential and magnetic field component measurement vectors (the vector elements correspond to measurements made at different sensor positions), respectively; $V_\infty \in R^p$ and $B_\infty \in R^q$ correspond to electric potential and magnetic field component values at the same sensor positions, and due to the same neuronal generators, in an infinite homogeneous medium; and $D \in R^{P \times P}$ and $E \in R^{q \times q}$ are transfer coefficient matrices, which define the anatomical deconvolution operator.

The anatomical deconvolution operator $\{D, E\}$ can be computed by the method and system described in CUBAN patent application 4/91, or alternatively by the new method described in the present invention. The descriptive parametric geometry is used for constructing a head phantom (9) with all the volume conductor properties of the experimental subject's head, said volume conductor properties consisting of the geometry and conductivity profile of the different constituent tissues (e.g., brain, skull, scalp). Electric potential (V) and magnetic field component (B) measurements are performed on the head phantom due to a plurality of implanted current dipoles or conductivity profiles (one at a time) with known locations and moments (dipoles located in the corresponding neural tissue volume). Also, theoretical EEG ($V\infty$) and MEG ($B\infty$) values are computed in the corresponding infinite homogeneous medium. The set of vectors $\{(V, B, V\infty, B\infty)\}$ (where $i = 1, 2, \ldots, N_d$, and $N_d$ is the number of implanted dipoles) is now used for computing the anatomical deconvolution operator $\{D, E\}$ in a least squares sense:

$$\underset{D}{\text{Min}}\left[\sum_i \|(V_\infty)_i - D(V)_i\|^2\right] \text{ And}$$

$$\underset{D}{\text{Min}}\left[\sum_i \|(B_\infty)_i - (B)_i - E(V)_i\|^2\right]$$

where $i = 1, 2, \ldots, N_d$ and $\|X\|$ denotes the norm of the vector X.

A further important use of the descriptive parametric geometry is the determination of anatomical and functional constraints for the localizations, orientations, activities, and connectivities of the brain electromagnetic waves generators (11) (generator constraints). Generator constraints are necessary for obtaining a unique inverse solution (14). For example, if the measured EEG and MEG activity is known beforehand to be generated only by cortical sources, then the generators can be located only on the cortical surface with orthogonal orientations.

Digital pre-processing (12) of the recorded EEG and MEG is necessary before proceeding to obtain inverse solutions. The two main steps consist of:

a) Artifact and noise elimination.

b) Separation of EEG and MEG samples related to fiducial markers (e.g. stimuli, subject's response, or spontaneous EEG and MEG events) for obtaining event related components (ERCs).

Statistical hypothesis tests are performed for determining the most adequate numerical description of the spatio-temporal properties of the stochastic ERCs in terms of sufficient statistics (13). The sufficient statistics can consist of cumulants of any order, or multiple time series parametric models, either in the time, frequency, or time-frequency domain. Alternatively, Karhunen-Loeve type representations can be used for fitting the sufficient statistics in stationary or non-stationary, linear or non-linear models.

The generator model for ERCs is:

$$V_t = \sum_k \phi_k M_k G_{kt} + E_{V_t} \text{ And } B_t = \sum_k \psi_k M_k G_{kt} + E_{B_t}$$

where the vectors $V_t \in R^p$ and $B_t \in R^q$ are the time (t) dependent electric potential and magnetic field component measurements, respectively; $\phi_k \in R^{P \times 3}$ and $\psi_k \in R^{q \times 3}$ denote the electric and magnetic transfer coefficient matrices for the k-th dipole source, respectively; $M_k \in R^3$ is the k-th dipole's moment; $g_{kt}$ is the time varying k-th dipole's intensity; $E_{V_t} \in R^p$ and $E_{B_t} \in R^q$ are noise vectors; $k = 1, 2, \ldots, N_d$ and $N_d$ is the number of dipole sources. This model has the following characteristics:

a) The ERCs are due to $N_d$ dipoles, with fixed positions and orientations, which may be known or unknown, and with unknown time varying dipole intensities. The dipole intensities are modeled as stochastic processes.

b) Measurements consist of the ERCs (due to dipoles as previously described) contaminated by additive noise. The additive noise is modeled as a stochastic process, not necessarily as spatio-temporal white noise. One particular model for the noise process allows for any general time-colored properties, with homogeneous isotropic spatial properties due to diffuse generators.

Inverse solutions (14) are computed for the source model in infinite homogeneous medium, based on the sufficient statistics of the measured data transformed to infinite homogeneous medium by means of the anatomical deconvolution operator (12), and taking into account the constraints imposed on the generators (11).

As a simple particular example, consider the zero mean linear stationary Gaussian case for spontaneous EEG activity, where the cross spectral matrices (frequency domain second order moments) constitute the sufficient statistics. Assuming that the ERCs concentrated generators and the noise diffuse generators are statistically independent, the model cross spectral matrix at frequency $\omega$ for the electric potential ($\Sigma_v$) is:

$$E_v = \phi M \Sigma_g M^* \phi^* + \Sigma_n$$

where $\Sigma_v \in C^{P \times P}$; $\phi \in R^{P \times (3N_d)}$, $\phi = (\phi_1 \phi_2 \cdots \phi_{N_d})$; $M \in R^{(3N_d) \times N_d}$, $$M = \begin{bmatrix} M_1 & 0 & 0 & \cdots & 0 \\ 0 & M_2 & 0 & \cdots & 0 \\ 0 & 0 & M_3 & & \cdot \\ 0 & 0 & 0 & & \cdot \\ \cdot & \cdot & \cdot & & \\ & & & & M_{N_d} \end{bmatrix};$$

$\Sigma_g \in C^{N_d \times N_d}$ is the generators cross spectral matrix; and $\Sigma_n \in R^{P \times P}$ is the pure real valued symmetric homogeneous isotropic noise cross spectral matrix, where, in the case of spherical geometry, $\Sigma n = \Sigma A_k P_k$, where the $A_k \geq 0$ are unknown coefficientsm, $[P_k]_{ij} = P_k(\cos(y_{ij}))$, $P_k$ being the Legendre polynominals of order k, and $y_{ij}$ is the angle between the i-th and j-th electrodes.

Inverse solutions can be obtained by at least squares criterion in which $\text{Tr}(\hat{\Sigma}_v - V - \Sigma_v)^2$ is minimized with respect to the dipole location parameters in matrix $\phi$, the dipole orientation parameters in matrix $M$, the generators cross spectral matrix $\Sigma_g$, and the coefficients $a_k$ of the noise cross spectral matrix, where $\hat{\Sigma}_v$ is the sample electric potential cross spectral matrix. Alternatively, inverse solutions can be obtained by maximizing the likelihoodfunction, which is equivalent to minimizing $\text{tr}(\Sigma_v^{-1}\hat{\Sigma}_v) - \det(\Sigma_v^{-1}\hat{\Sigma}_v)$. Independently of the estimation method used, the inverse solutions must be obtained under the generator constraints. Once the locations and orientations of the ERCs dipoles are estimated, their activities $G_t^* = (g_1 + g_2 + \cdot\cdot g_{Ndt})$ can be estimated at each time instant as:

$$\hat{G}_t = (\hat{M}^* \hat{\phi}^* \Sigma_n^{-1} \hat{\phi} \hat{M})^{-1} (\hat{M}^* \hat{\phi}^* \Sigma_n^{0-1}) V_t$$

which is obtained by either maximum likelihood or weighted least squares methods.

Summarizing the inverse solution example previously described, the following generator characteristics were computed for a given number of dipoles and a given number of coefficients $a_k$ in the expansion of the noise cross spectral matrix:

a) The activity $k_t$ for each dipole k, at each time instant t.

b) The connectivities $\Sigma_v$ between all pairs of dipoles.

c) The locations ($\phi$) and orientations ($M$) of the dipoles.

d) The expansion coefficients of the homogeneous isotropic noise cross spectral matrix.

Tests for inverse solution uniqueness (15) must be made before performing estimations, since under non-uniqueness, computations may render meaningless results. Uniqueness may be achieved by setting more severe generator constraints, or by decreasing the number of dipoles until the model is identifiable.

Once the generator characteristics are estimated, a test for the goodness of fit of the inverse solution is performed (16). Also, hypotheses concerning if a given generator has significant activity, or if the connectivity between a pair of generators is significant, can also be tested (16). In all cases statistical hypothesis testing is based on resampling techniques such as Montecarlo, the Jackknife, and the Bootstrap.

The estimated localizations, orientations, activities, and connectivities of the ERCs generators of an experimental subject are compared with those of a normal population (17), by means of multivariate metrics for measuring distances between estimators and normative data of a sample from the normal population, taking properly into account the effect of covariables such as age in order to decrease metric variability.

Finally, visual displays (18) are presented in the form of three dimensional and two dimensional images of the head, where the localizations, orientations, activities, and connectivities of the ERCs generators are displayed by coding their numerical values in terms of color, intensity, and graphical icons, and where optionally, the multivariate metrics corresponding to comparison with norms can also be displayed by superposition.

Figure 2:
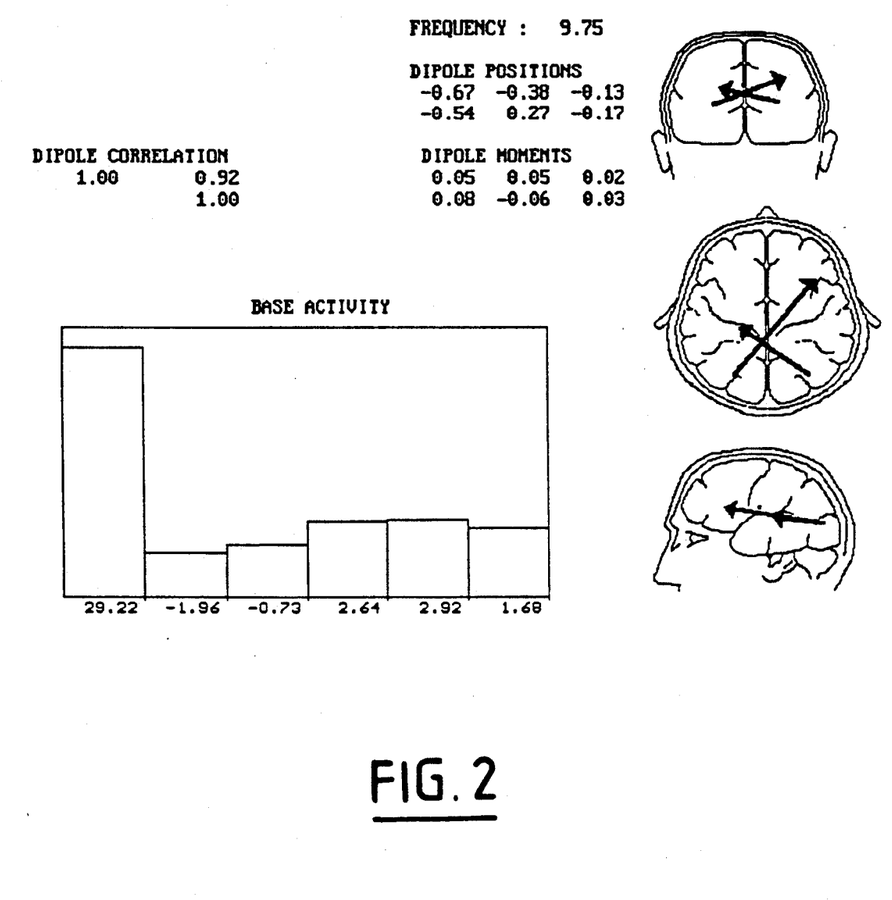
FIG. 2) illustrates an example of a visual display of the characteristics of diffuse and concentrated generators in a normal experimental subject.

FIG. 2 illustrates a visual display of an inverse solution obtained from a normal experimental subject, based on a spontaneous EEG recording under eyes closed, awake, conditions. The sufficient statistics used was the cross spectral matrix at the alpha peak maximum (w=9.75 Hz). Two dipoles were fitted, together with additive uncorrelated homogeneous isotropic spatial noise. Generators are represented as arrows in the three head views (back, top, and left views). Generator localization and moments are given in cartesian coordinates referred to a unit radius sphere, with z axis coming out through the vertex, x axis coming out through nasion, and y axis coming out through the left ear (T3 electrode position). connectivities are given in terms of the generator correlation matrix. Noise characteristics are illustrated as "BASE ACTIVITY", giving the values of the expansion coefficients of the homogeneous isotropic process. Note the alpha rhythm generators located in the occipital cortex.

Figure 3:
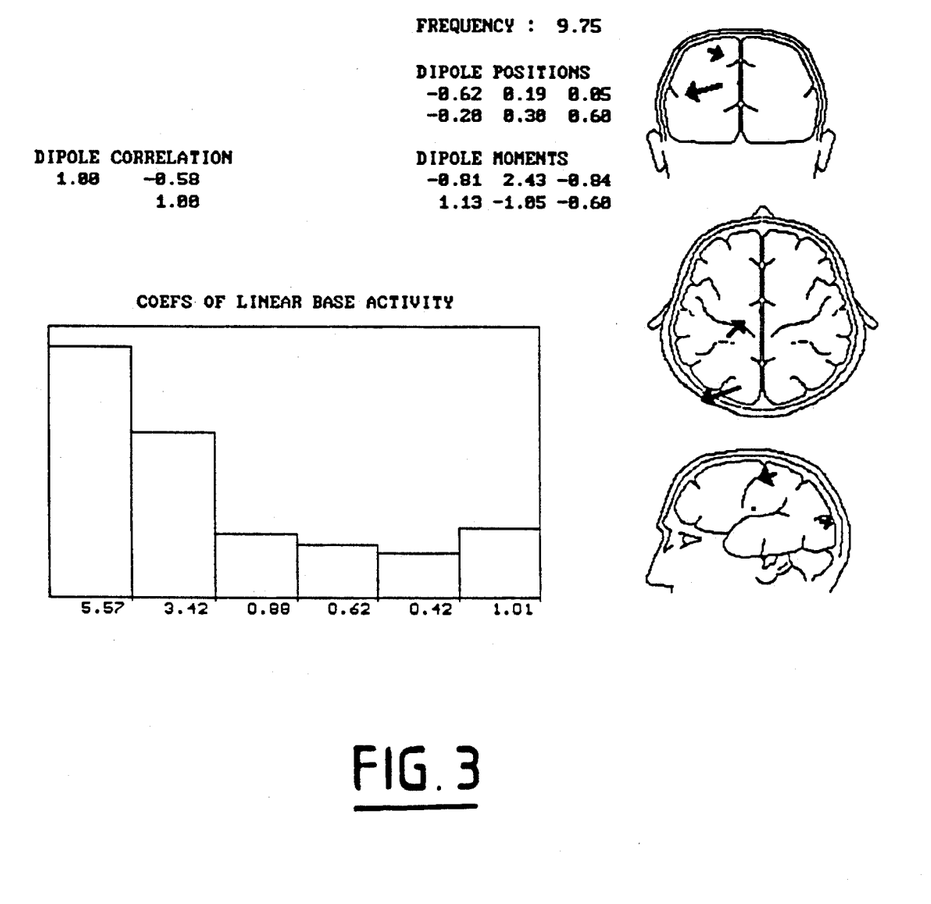
FIG. 3) illustrates an example of visual display of the characteristics of diffuse and concentrated generators in a patient with a cerebrovascular accident.

FIG. 3 illustrates a visual display of an inverse solution obtained from an experimental subject with a lateralized right cerebrovascular accident, based on a spontaneous EEG recording under eyes closed, awake, conditions. Analysis procedures were the same to those used for the normal subject of FIG. 2. Note that only one alpha generator lies in the normal position (left occipital cortex).

We claim:

1. A method for three dimensional tomography of activity and connectivity of brain electromagnetic waves generators, said method including the steps of:

a) positioning a set of electrodes and magnetic sensors to detect and record brain electromagnetic signals representing physiological activity in the form of an electroencephalogram (EEG) and a magnetoencephalogram (MEG), and measuring exact positions of the electrodes and sensors with respect to a reference coordinate system determined by certain anatomical landmarks of a head of an experimental subject;

b) amplifying the electromagnetic signals detected at each electrode and sensor by connecting an amplifier to each electrode and sensor;

c) obtaining on-line digital spatio-temporal signals, consisting of said EEG and MEG, by connecting analog-digital converters to each amplifier, and digitizing all data as it is gathered;

d) determining a parametric description for an anatomy of the experimental subject's head to obtain a descriptive parametric geometry;

e) using said descriptive parametric geometry for constructing a head phantom with volume conductor properties of the experimental subject's head;

f) performing EEG and MEG measurements on said head phantom due to known current dipoles located in a corresponding neural tissue volume, for determining a linear operator which transforms original EEG and MEG measurements into equivalent infinite homogeneous medium measurements (anatomical deconvolution);

g) using said descriptive parametric geometry for determining anatomical and functional constraints for localizations, orientations, activities, and connectivities of the brain electromagnetic waves generators (generator constraints);

h) digitally pre-processing the EEG and MEG for artifact and noise elimination, and for separation of EEG and MEG samples related to said fiducial markers, for obtaining event related components (ERCs);

i) statistically analyzing said ERCs for determining the most adequate numerical description of spatiotemporal properties in terms of sufficient statistics;

j) computing activities and connectivities of the ERCs generators, based on a static solution to an inverse electromagnetic problem, under said generator constraints, using sufficient statistics for the ERCs transformed to an infinite homogeneous medium by means of said anatomical deconvolution;

k) in case said generator constraints do not allow a unique solution to the inverse problem, decreasing a number of ERCs generators sufficiently to allow for proper identifiability of the inverse problem;

l) statistically evaluating a goodness of fit of the static solution, taking into account an existence of colored spatial and temporal noise, and including statistical hypotheses for testing an absence of activity and connectivity of the ERCs generators; and m) visually displaying three dimensional and two dimensional images corresponding to the localizations, orientations, activities, and connectivities of the ERCs generators.

2. A method as claimed in claim 1 wherein events are detected in the EEG and MEG for recording and modification of an experimental sequence.

3. A method as claimed in claim 2 wherein said events are defined deterministically.

4. A method as claimed in claim 2 wherein said events are defined statistically.

5. A method as claimed in claim 2 wherein said events are determined in terms of fuzzy logic.

6. A method as claimed in claim 2 wherein said events are paroxistic events.

7. A method as claimed in claim 2 wherein said events are alpharhythmic desynchronization events.

8. A method as claimed in claim 1 wherein series expansions are established in terms of three dimensional basis functions for the description of contours, physical properties, and metabolic properties of the head, producing a descriptive parametric geometry consisting of sets of expansion coefficients for the basis function.

9. A method as claimed in claim 1 wherein the descriptive parametric geometry establishes a priori constraints on said localizations and orientations of the ERCs generators.

10. A method as claimed in claim 1 wherein the descriptive parametric geometry is used for constructing the head phantom with all of said volume conductor properties of the experimental subject's head.

11. A method as claimed in claim 1 wherein EEG and MEG measurements are performed on the head phantom, using established current dipoles located in the corresponding neural tissue volume, with known locations, orientations and activities, where theoretical EEG and MEG values are computed in the corresponding infinite homogeneous medium, and where the linear operator in matrix form which transforms original EEG and MEG measurements into equivalent infinite homogeneous medium measurements is computed in a least squares sense, thus defining an anatomical deconvolution operation.

12. A method as claimed in claim 1 wherein event related samples (ERSs) of said EEG and MEG are separated according to different types of fiducial markers, and wherein said ERSs contain ERCs, which are estimated under the assumption that a set of generators of the ERCs of said ERSs have fixed localizations and orientations, and stochastic activities and connectivities.

13. A method as claimed in claim 1 wherein statistical hypothesis tests are used for determining a set of sufficient statistics for the description of the ERCs, where said set of sufficient statistics consist of cumulants of any order, in any domain.

14. A method as claimed in claim 1 wherein the ERSs are modeled as containing additive noise due to the activity of diffuse generators independent of ERCs concentrated generators, said diffuse generators having the properties of a stochastic process.

15. A method as claimed in claim 1 wherein the inverse problem is solved for the activities and connectivities of neuronal generators, based on all the information provided by ERCs sufficient statistics, under the generator constraints on localizations and orientations provided by the descriptive parametric geometry, for infinite homogeneous medium measurements obtained by applying an anatomical deconvolution operator.

16. A method as claimed in claim 1 wherein the goodness of fit of the estimated inverse solution and tests of hypotheses on no activity of the ERCs generators examined based on statistical resampling techniques.

17. A method as claimed in claim 1 wherein the estimated localizations, orientations, activities, and connectivities of the ERCs generators of an experimental subject are compared with those of a normal population by means of multivariate metrics for measuring distances between estimators and normative data of a sample from the normal population, taking into account an effect of convariables in order to decrease metric variability.

18. A method as claimed in claim 1 wherein visual displays are presented in the form of three dimensional and two dimensional images of the head, where the localizations, orientations, activities, and connectivities of the ERCs generators are displayed by coding their numerical values in terms of color, intensity, and graphical icons.

19. A method as claimed in 18 wherein multivariate metrics corresponding to comparison with norms are also displayed by superposition.

20. A method as claimed in claim 1 further comprising the step of pre visual, auditory, and somato-sensorial stimulation to the experimental subject during said recording of the EEG and MEG, carried out under control of said central experimental program.

21. A method as claimed in claim 20 further comprising the step of identifying responses produced by the experimental subject during said EEG and MEG recording, inclusion of fiducial markers of the type and time of stimulation in said recording, and modifying an experimental program sequence based on the responses produced by the experimental subject.

22. A method as claimed in claim 21 further comprising the step of including fiducial markers in said recording for the time and type of spontaneous events detected in the EEG and MEG produced by the experimental subject during recording, and modifying the central experimental program based on the spontaneous events.

23. A method as claimed in claim 1 wherein step d) comprises the step of determining the parametric geometry for the anatomy of the experimental subject's head by means of exact computations based on image processing of the subject's head.

24. A method as claimed in claim 1 wherein step d) comprises the step of determining the parametric description for the anatomy of the experimental subject's head based on approximate computations based on a small set of anatomical measurements and comparison with a data base of normal and abnormal variability.

25. A method as claimed in claim 1 further comprising the step of computing multivariate distances between ERC generators characteristic of said experimental subject and of a normal population as determined by a normative data-base.

26. A method as claimed in claim 25 further comprising the step of displaying said multivariate distances.

27. A method as claimed in claim 1 further comprising the step of presenting stimulation sequences to the subject in the form of computerized video-games, and recording responses to the video-games.

28. A method as claimed in claim 1 wherein the descriptive parametric geometry is obtained from functional images of the experimental subject's head.

29. A method as claimed in claim 1 wherein the descriptive parametric geometry is obtained from a minimum set of easily measured parameters which can be used to statistically predict the descriptive parametric geometry via information contained in a normative data base with a representative sample covering a typical population.

30. A method as claimed in claim 1 wherein EEG and MEG values are theoretically computed on a head phantom defined by the descriptive parametric geometry using established current dipoles located in corresponding neural tissue volume, with known locations, orientations, and activities, and wherein the theoretical EEG and MEG values are computed in the corresponding infinite homogeneous medium, and wherein a linear operator in matrix form which transforms original EEG and MEG measurements into equivalent infinite homogeneous medium measurements is computed in a least squares sense, thus defining an anatomical deconvolution operation.

31. A method as claimed in claim 1 wherein statistical hypothesis tests are used for determining a set of sufficient statistics for a description of stochastic event related samples (ERSs), wherein said set of sufficient statistics consists of multiple time series parametric models, in a domain selected from the group consisting of the time, frequency, and time-frequency domains.

32. A system for the three dimensional tomography of activity and connectivity of brain electromagnetic waves generators comprising:
   a) A set of electrodes and magnetic sensors adapted to be positioned to detect brain electromagnetic signals representative of physiological activity in the form of an electroencephalogram (EEG) and a magnetoencephalogram (MEG), and means for measuring exact positions of the electrodes and sensors with respect to a reference coordinate system determined by certain anatomical landmarks of a head of an experimental subject.
   b) Means for amplification of said electromagnetic signals detected at each electrode and sensor;
   c) Means for obtaining on-line digital spatio-temporal signals consisting of said EEG and MEG;
   d) Means for the presentation of visual, auditory, and somato-sensorial stimulation to the experimental subject during EEG and MEG recording;
   e) Means for recording vocal or movement responses produced by the experimental subject during EEG and MEG recording;
   f) A central digital computer subsystem, comprising:
   means for reading the experimental subject's image data, and means for computing and storing a descriptive parametric geometry, an anatomical deconvolution operator, and generator constraints;
   means for constructing a head phantom based on the descriptive parametric geometry, and means for the implantation of current dipoles in a corresponding neural tissue volume of the phantom;
   means controlling experiments including means for causing stimulation of the experimental subject, recording of the subject's responses, detection and recording of special EEG and MEG events, and simultaneous recording of said electromagnetic signals;
   means for pre-processing the recorded electromagnetic signals for artifact and noise elimination;
   means for estimating event related components (ERCs)
   means for computing sufficient statistics of the ERCs;
   means for estimating an additive non-white spatio-temporal noise due to diffuse generators;
   means for performing tests of hypothesis about the goodness of fit of an estimated inverse solution;
   means for estimating localizations, orientations, activities, and connectivities of generators of the ERCs;
   means for comparing characteristics of the ERCs generators with a normative data base and means for computing multivariate metrics;
   means for the visual display of ERCs generators characteristics and of the multivariate metrics.

33. A system as claimed in claim 32 wherein said central digital computer subsystem includes a multitasking processor.

34. A system as claimed in claim 32 wherein said central digital computer subsystem includes a set of distributed processors.

35. A system as claimed in claim 32 wherein said means for reading the experimental subject's image data comprises means for reading images selected from the group consisting of CAT scan images, NMR images, PET images, and anatomical measurements.

* * * * *